United States Patent
Xu

(10) Patent No.: US 11,279,815 B2
(45) Date of Patent: Mar. 22, 2022

(54) COMPOSITIONS AND METHODS FOR IMPROVING POLYMER FLOW RATE

(71) Applicant: Inovia Materials LLC, Greenwood Village, CO (US)

(72) Inventor: Yanjie Xu, Greenwood Village, CO (US)

(73) Assignee: Inovia Materials LLC, Greenwood Village, CO (US)

( * ) Notice: Subject to any disclaimer, the term of this patent is extended or adjusted under 35 U.S.C. 154(b) by 0 days.

(21) Appl. No.: 16/791,601

(22) Filed: Feb. 14, 2020

(65) Prior Publication Data

US 2021/0253827 A1    Aug. 19, 2021

(51) Int. Cl.
| | |
|---|---|
| *C08K 5/50* | (2006.01) |
| *C07C 211/63* | (2006.01) |
| *C07D 233/58* | (2006.01) |
| *C07F 9/54* | (2006.01) |
| *C08J 3/20* | (2006.01) |
| *C08K 5/3445* | (2006.01) |
| *C08K 5/521* | (2006.01) |

(52) U.S. Cl.
CPC .............. *C08K 5/50* (2013.01); *C07C 211/63* (2013.01); *C07D 233/58* (2013.01); *C07F 9/5407* (2013.01); *C07F 9/5442* (2013.01); *C08J 3/203* (2013.01); *C08K 5/3445* (2013.01); *C08K 5/521* (2013.01)

(58) Field of Classification Search
CPC ........ C08K 5/50; C08K 5/3445; C08K 5/521; C07C 211/63; C07D 233/58; C07F 9/5407; C07F 9/5442; C08J 3/203
See application file for complete search history.

(56) References Cited

U.S. PATENT DOCUMENTS

| | | | | |
|---|---|---|---|---|
| 4,279,799 | A | * 7/1981 | MacGregor | ............. C08K 7/14 524/449 |
| 6,417,255 | B1 | 7/2002 | Penning et al. | |
| 2001/0016626 | A1 | 8/2001 | Vollenberg et al. | |
| 2002/0132889 | A1 | 9/2002 | Penning | |
| 2003/0211320 | A1 * | 11/2003 | Thompson | ............... C09D 5/00 428/375 |
| 2006/0100326 | A1 * | 5/2006 | Kawakabe | ........... C08K 5/0075 524/115 |
| 2011/0073331 | A1 * | 3/2011 | Xu | ...................... D06M 13/244 169/46 |
| 2015/0291776 | A1 * | 10/2015 | Kim | ........................ C08L 77/06 524/168 |

FOREIGN PATENT DOCUMENTS

| | | | | |
|---|---|---|---|---|
| JP | 2014015610 | * | 1/2014 | ............. C08J 11/28 |
| WO | 2007/143525 | | 12/2007 | |
| WO | 2015/157051 | | 10/2015 | |

OTHER PUBLICATIONS

English machine translation of JP 2014-015610. (Year: 2014).*
European Search Report for Application No. 20167296.1 dated Jul. 30, 2020.

* cited by examiner

*Primary Examiner* — John E Uselding
(74) *Attorney, Agent, or Firm* — Thomas | Horstemeyer LLP

(57) ABSTRACT

The present disclosure provides a polymeric composition including a thermoplastic polymer and an ionic liquid compound, wherein the ionic liquid compound improves the melt flow rate of the polymeric composition. The present disclosure also provides a method of preparing a polymeric composition with improved melt flow rate by mixing an ionic liquid compound with a thermoplastic polymer to obtain the polymeric composition.

7 Claims, No Drawings

COMPOSITIONS AND METHODS FOR IMPROVING POLYMER FLOW RATE

FIELD OF INVENTION

The disclosure relates to compositions and methods for improving polymer melt flow rate.

BACKGROUND

Flow improvers are important additives in polymer industry. They enable polymers to be processed and recycled at a lower temperature and in a more efficient manner. Flow improvers can also help achieve a smoother surface, and lower the defect rate of the polymer product. A good melt flow behavior allows fast molding cycles and complex mold making.

SUMMARY

In one aspect, the present disclosure provides a method of preparing a polymeric composition with improved melt flow rate including the steps of: mixing between about 70 wt % and about 99.99 wt % of a thermoplastic polymer with between about 0.01 wt % and about 30 wt % of a compound having the formula (I)

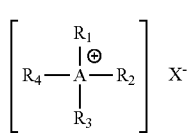

wherein A is P or N,
when A is P,
    each of $R_1$, $R_2$, $R_3$ and $R_4$ is independently selected from the group consisting of $(C_1\text{-}C_{20})$alkyl, aryl, $(C_3\text{-}C_{10})$heterocyclyl, $(C_3\text{-}C_{10})$cycloalkyl, $(C_3\text{-}C_{10})$heterocyclyl$(C_1\text{-}C_8)$ alkyl, aryl$(C_1\text{-}C_8)$alkyl, heteroaryl and heteroaryl$(C_1\text{-}C_8)$alkyl that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCOO]^-$, $[NO_3]^-$, $[PF_6]^-$, $[BF_4]^-$, $(RSO_2)_2N^-$ oxalate, dicarboxylate and tricarboxylate, formate, phosphate, and aluminate, wherein each R is independently selected from the group consisting of $(C_1\text{-}C_{20})$alkyl, aryl, $(C_3\text{-}C_{10})$heterocyclyl, $(C_3\text{-}C_{10})$cycloalkyl, $(C_3\text{-}C_{10})$heterocyclyl$(C_1\text{-}C_8)$alkyl, aryl$(C_1\text{-}C_8)$alkyl, heteroaryl and heteroaryl$(C_1\text{-}C_8)$alkyl group that may be unsubstituted or substituted by halogen, nitro, methoxy, carboxy, —$NH_2$, —OH, —SH, —$NHCH_3$, —$N(CH_3)_2$, —SMe and cyano;

when A is N,
    each of $R_1$, $R_2$, $R_3$ and $R_4$ is independently selected from the group consisting of hydrogen, $(C_1\text{-}C_{20})$alkyl, aryl, $(C_3\text{-}C_{10})$heterocyclyl, $(C_3\text{-}C_{10})$cycloalkyl, $(C_3\text{-}C_{10})$heterocyclyl$(C_1\text{-}C_8)$alkyl, aryl$(C_1\text{-}C_8)$alkyl, heteroaryl and heteroaryl$(C_1\text{-}C_8)$alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, or

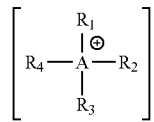

is a heterocyclyl or a heteroaryl ring containing nitrogen, wherein the heterocyclyl or the heteroaryl ring is optionally substituted by a substitution selected the group consisting of $(C_1\text{-}C_{20})$alkyl, aryl, $(C_3\text{-}C_{10})$heterocyclyl, $(C_3\text{-}C_{10})$cycloalkyl, $(C_3\text{-}C_{10})$ heterocyclyl $(C_1\text{-}C_8)$alkyl, aryl$(C_1\text{-}C_8)$alkyl, heteroaryl and heteroaryl$(C_1\text{-}C_8)$alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, $X^-$ is selected from the group consisting of halide, $[B(R)_4]^-$, $OH^-$, $SCN^-$, $RPO_4^-$, $(RO)_2P(=O)O^-$, $RSO_3^-$, $RSO_4^-$, $ROSO_3^-$, $[N(CN)_2]RCOO^-$, $NO_3^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1\text{-}C_{20})$alkyl, aryl, $(C_3\text{-}C_{10})$heterocyclyl, $(C_3\text{-}C_{10})$cycloalkyl, $(C_3\text{-}C_{10})$heterocyclyl$(C_1\text{-}C_8)$alkyl, aryl$(C_1\text{-}C_8)$alkyl, heteroaryl and heteroaryl$(C_1\text{-}C_8)$alkyl group that may be unsubstituted or substituted by halogen, nitro, methoxy, carboxy, —$NH_2$, —OH, —SH, —$NHCH_3$, —$N(CH_3)_2$, —SMe and cyano;

wherein the polymeric composition has a melt flow rate higher than that of the thermoplastic polymer.

In another aspect, the present disclosure provides polymeric composition including between about 70 wt % and about 99.99 wt % of a thermoplastic polymer; and between about 0.01 wt % and about 30 wt % of a compound having the formula of

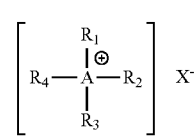

wherein A is P or N;
when A is P,
    each of $R_1$, $R_2$, $R_3$ and $R_4$ is independently selected from the group consisting of $(C_1\text{-}C_{20})$alkyl, aryl, $(C_3\text{-}C_{10})$heterocyclyl, $(C_3\text{-}C_{10})$cycloalkyl, $(C_3\text{-}C_{10})$heterocyclyl$(C_1\text{-}C_8)$ alkyl, aryl$(C_1\text{-}C_8)$alkyl, heteroaryl and heteroaryl$(C_1\text{-}C_8)$alkyl that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCOO]^-$, $[NO_3]^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1\text{-}C_{20})$alkyl, aryl, $(C_3\text{-}C_{10})$heterocyclyl, $(C_3\text{-}C_{10})$cycloalkyl, $(C_3\text{-}C_{10})$heterocyclyl$(C_1\text{-}C_8)$alkyl, aryl$(C_1\text{-}C_8)$alkyl, heteroaryl and heteroaryl$(C_1\text{-}C_8)$alkyl that may be unsubstituted or substituted by halogen, nitro, methoxy, carboxy, —$NH_2$, —OH, —SH, —$NHCH_3$, —$N(CH_3)_2$, —SMe and cyano;

when A is N,
each of $R_1$, $R_2$, $R_3$ and $R_4$ is independently selected from the group consisting of hydrogen, $(C_1-C_{20})$alkyl, aryl, $(C_3-C_{10})$heterocyclyl, $(C_3-C_{10})$cycloalkyl, $(C_3-C_{10})$heterocyclyl$(C_1-C_8)$alkyl, aryl$(C_1-C_8)$alkyl, heteroaryl and heteroaryl$(C_1-C_8)$alkyl group that may be unsubstituted or substituted by halogen, nitro, trifluoromethyl, trifluoromethoxy, methoxy, carboxy, —NH$_2$, —OH, —SH, —NHCH$_3$, —N(CH$_3$)$_2$, cyano, —SMe, and —SO$_3$H, or

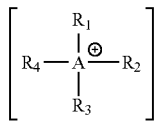

is a heterocyclyl or a heteroaryl containing nitrogen, wherein the heterocyclyl or the heteroaryl ring is optionally substituted by a substitution selected the group consisting of $(C_1-C_{20})$alkyl, aryl, $(C_3-C_{10})$heterocyclyl, $(C_3-C_{10})$cycloalkyl, $(C_3-C_{10})$ heterocyclyl $(C_1-C_8)$alkyl, aryl$(C_1-C_8)$alkyl, heteroaryl and heteroaryl $(C_1-C_8)$alkyl group that may be unsubstituted or substituted by halogen, nitro, trifluoromethyl, trifluoromethoxy, methoxy, carboxy, —NH$_2$, —OH, —SH, —NHCH$_3$, —N(CH$_3$)$_2$, cyano, —SMe, and —SO$_3$H, $X^-$ is selected from the group consisting of halide, $[B(R)_4]^-$, $OH^-$, $SCN^-$, $RPO_4^-$, $(RO)_2P(=O)O^-$, $RSO_3^-$, $RSO_4^-$, $ROSO_3^-$, $[N(CN)_2]^-$, $RCOO^-$, $NO_3^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, $(C_3-C_{10})$heterocyclyl, $(C_3-C_{10})$cycloalkyl, $(C_3-C_{10})$heterocyclyl $(C_1-C_8)$alkyl, aryl$(C_1-C_8)$alkyl, heteroaryl and heteroaryl$(C_1-C_8)$alkyl group that may be unsubstituted or substituted by halogen, nitro, methoxy, carboxy, —NH$_2$, —OH, —SH, —NHCH$_3$, —N(CH$_3$)$_2$, —SMe and cyano;

wherein the thermoplastic polymer is a high temperature polymer selected from the group consisting of polyamides, polyamideimides, polysulfones, polyethersulfones, polyarylsulfones, poly ketones, polyphenylsulfones, polyetherimides, polyetherketones, polyphenylene sulfoxide, and combinations thereof; or the thermoplastic polymer is a thermoplastic elastomer selected from the group consisting of thermoplastic polyurethanes, thermoplastic copolyester, thermoplastic polyamides, and combinations thereof;

wherein the polymeric composition has a melt flow rate higher than that of the thermoplastic polymer.

DETAILED DESCRIPTION

Provided are compositions and methods for improving polymer melt flow rate. The present disclosure provides a polymeric composition including a thermoplastic polymer and an ionic liquid compound, wherein the ionic liquid compound improves the melt flow rate of the polymeric composition. The present disclosure also provides a method of preparing a polymeric composition with improved melt flow rate by mixing an ionic liquid compound with a thermoplastic polymer to obtain the polymeric composition.

For convenience, before further description of the present invention, certain terms used in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

The term "about" herein is used to indicate that a value includes the inherent variation of error for the device, the method being employed to determine the value, or the variation that exists among the study subjects.

The terms "optional" and "optionally" as used herein mean that the subsequently described event or circumstance may or may not occur, and that the description includes instances where the event or circumstance occurs and instances in which it does not. For example, "optionally substituted aryl" encompasses both "aryl" and "substituted aryl" as defined herein.

The term "alkyl" as used herein refers to a linear or branched saturated hydrocarbon. Examples of alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (tert-butyl), pentyls, hexyls, octyls, and decyls. In some embodiments, an alkyl group has from 1 to 10 carbon atoms, from 1 to 6 carbon atoms, or from 1 to 4 carbon atoms.

The term "aryl" as used herein refers to a monocyclic aromatic hydrocarbon group or a multicyclic group that contains at least one aromatic hydrocarbon ring. In certain embodiments, an aryl group has from 6 to 15 or more, or 6 to 12 or more, or 6 to 10 or more, ring atoms. Examples of aryl groups include, but are not limited to, phenyl, naphthyl, fluorenyl, azulenyl, anthryl, phenanthryl, biphenyl and terphenyl. The aromatic hydrocarbon ring of an aryl group may be attached or fused to one or more saturated, partially unsaturated, or aromatic rings—e.g., dihydronaphthyl, indenyl, indanyl and tetrahydronaphthyl (tetralinyl). An aryl group may optionally be substituted with one or more substituents as described herein.

The term "cycloalkyl" as used herein refers to a saturated or unsaturated monocyclic, bicyclic, other multicyclic, or bridged cyclic hydrocarbon group. A cycloalkyl group can have 3-22, 3-12, or 3-8 ring carbons, referred to herein as $(C_3-C_{22})$cycloalkyl, $(C_3-C_{12})$cycloalkyl, or $(C_3-C_8)$cycloalkyl, respectively. A cycloalkyl group can also have one or more carbon-carbon double bond or carbon-carbon triple bond.

The term "heterocyclyl", "heterocycle" or "heterocyclic" refers to cyclic groups containing at least one heteroatom as a ring atom. In some embodiments, the heterocyclyl, heterocycle or heterocyclic group includes 1 to 3 heteroatoms as ring atoms, with the remainder of the ring atoms being carbon atoms. Examples of heteroatoms include oxygen, sulfur, and nitrogen. In some embodiments, the heterocycle may be 3- to 10-membered ring structures or 3- to 7-membered rings, whose ring structures include one to four heteroatoms. The "heterocyclyl", "heterocycle" or "heterocyclic" may be a single saturated or partially unsaturated non-aromatic ring or a non-aromatic multiple ring system. Examples of heterocycles include, but are not limited to, azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, A-bromopyrrolidine, and N-chloropiperidine.

The term "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaryl" as used herein represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring. Examples of heteroaryl groups include, but are not limited to, acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, and xanthene.

All numerical ranges herein include all numerical values and ranges of all numerical values within the recited range of numerical values. As a non-limiting example, $(C_1-C_6)$ alkyls also include any one of $C_1$, $C_2$, $C_3$, $C_4$, $C_5$, $C_6$, $(C_1-C_2)$, $(C_1-C_3)$, $(C_1-C_4)$, $(C_1-C_5)$, $(C_2-C_3)$, $(C_2-C_4)$, $(C_2-C_5)$, $(C_2-C_6)$, $(C_3-C_4)$, $(C_3-C_5)$, $(C_3-C_6)$, $(C_4-C_5)$, $(C_4-C_6)$, and $(C_5-C_6)$ alkyls.

The terms "halo", "halide" and "halogen" as used herein refer to an atom selected from fluorine, chlorine, bromine, and iodine.

The term "engineering plastics" as used herein refers to a group of plastic materials that have better mechanical and/or thermal properties than the more widely used commodity plastics. In some embodiments, "engineering plastics" refers to thermoplastic materials rather than thermosetting ones. Examples of engineering plastics include, but are not limited to, acrylonitrile-butadiene styrene (ABS), polycarbonates and polyamides (nylons).

The term "thermoplastic elastomer" as used herein refers to polymers that are both thermoplastic and elastomeric. Examples of thermoplastic elastomers, include but are not limited to, a polystyrene-based elastomer (soft segment: polybutadiene, polyisoprene/hard segment: polystyrene), a polyolefin-based elastomer (soft segment: ethylene propylene rubber/hard segment: polypropylene), a polyvinyl chloride-based elastomer (soft segment: polyvinyl chloride/hard segment: polyvinyl chloride), a polyurethane-based elastomer (soft segment: polyether, polyester, or polycarbonate/hard segment: polyurethane), a polyester-based elastomer (soft segment: aliphatic polyester/hard segment: aromatic polyester), a polyether ester-based elastomer (soft segment: polyether/hard segment: polyester), a polyamide-based elastomer (soft segment: polypropylene glycol, polytetramethylene ether glycol, polyester, or polyether/hard segment: polyamide (such as a nylon resin)), a polybutadiene-based elastomer (soft segment: amorphous butyl rubber/hard segment: syndiotactic 1,2-polybutadiene resin), an acrylic elastomer (soft segment: polyacrylate ester/hard segment: polymethyl methacrylate). It is to be noted that the thermoplastic elastomers described herein may be used solely or may be used in combination of two or more thereof.

The term "high temperature polymer" or "high temperature plastic" refers to polymers or plastics that exhibit the property of stability at high temperatures.

As used herein, the term "melt flow rate" or "melt flow index" refers to a measure of the ease of flow of a thermoplastic polymer melt, which includes a polymer composition melt. It is defined as the mass of polymer, in grams, flowing in ten minutes through a capillary of a specific diameter and length by a pressure applied via prescribed alternative gravimetric weights at alternative prescribed temperatures. The method is described in the standard ASTM D1238-04.

The present disclosure provides compositions and methods for improving polymer flow rate. Adding an ionic liquid to a polymer may improve the polymer's melt flow index.

In one aspect, the present disclosure provides a polymeric composition including a thermoplastic polymer and an ionic liquid. In one embodiment, the present disclosure provides a polymeric composition including between about 70 wt % and about 99.99 wt % of a thermoplastic polymer; and between about 0.01 wt % and about 30 wt % of a compound having the formula (I):

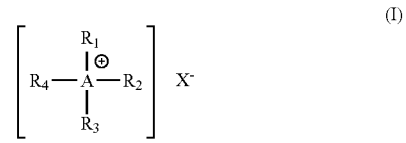

wherein A is P or N;
$X^-$ is selected from the group consisting of halide, $[B(R)_4]^-$, $OH^-$, $SCN^-$, $RPO_4^-$, $(RO)_2P(=O)O^-$, $RSO_4^-$, $RSO_4^-$, $ROSO_3^-$, $[N(CN)_2]^-$, $RCOO^-$, $NO_3^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, $(C_3-C_{10})$heterocyclyl, $(C_3-C_{10})$cycloalkyl, $(C_3-C_{10})$heterocyclyl$(C_1-C_8)$alkyl, aryl$(C_1-C_8)$alkyl, heteroaryl and heteroaryl$(C_1-C_8)$alkyl group that may be unsubstituted or substituted by halogen, nitro, methoxy, carboxy, $-NH_2$, $-OH$, $-SH$, $-NHCH_3$, $-N(CH_3)_2$, $-SMe$ and cyano;
when A is P,
each of $R_1$, $R_2$, $R_3$ and $R_4$ is independently selected from the group consisting of $(C_1-C_{20})$alkyl, aryl, $(C_3-C_{10})$heterocyclyl, $(C_3-C_{10})$cycloalkyl, $(C_3-C_{10})$heterocyclyl $(C_1-C_8)$ alkyl, aryl$(C_1-C_8)$alkyl, heteroaryl and heteroaryl$(C_1-C_8)$alkyl that may be unsubstituted or substituted by halogen, nitro, trifluoromethyl, trifluoromethoxy, methoxy, carboxy, $-NH_2$, $-OH$, $-SH$, $-NHCH_3$, $-N(CH_3)_2$, cyano, $-SMe$, and $-SO_3H$,
when A is N,
each of $R_1$, $R_2$, $R_3$ and $R_4$ is independently selected from the group consisting of hydrogen, $(C_1-C_{20})$alkyl, aryl, $(C_3-C_{10})$heterocyclyl, $(C_3-C_{10})$cycloalkyl, $(C_3-C_{10})$heterocyclyl$(C_1-C_8)$alkyl, aryl$(C_1-C_8)$alkyl, heteroaryl and heteroaryl $(C_1-C_8)$alky 1 group that may be unsubstituted or substituted by halogen, nitro, trifluoromethyl, trifluoromethoxy, methoxy, carboxy, $-NH_2$, $-OH$, $-SH$, $-NHCH_3$, $-N(CH_3)_2$, cyano, $-SMe$, and $-SO_3H$, or

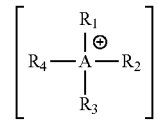

is heterocyclyl or a heteroaryl ring containing nitrogen, wherein the heterocyclyl or the heteroaryl ring is optionally substituted by a substitution selected the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$) heterocyclyl ($C_1$-$C_8$)alkyl, aryl($C_1$-$C_8$)alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$.

In one embodiment, when A is P, $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCOO]^-$, $[NO_3]^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$)heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, methoxy, carboxy, —$NH_2$, —OH, —SH, —$NHCH_3$, —$N(CH_3)_2$, —SMe and cyano.

In one embodiment, the polymeric composition has a melt flow rate higher than that of the thermoplastic polymer.

In one embodiment, the compound is an ionic liquid.

In one embodiment, thermoplastic polymer is a high temperature polymer selected from the group consisting of polyamides, polyamideimides, polysulfones, polyethersulfones, polyarylsulfones, poly ketones, polyphenylsulfones, polyetherimides, polyetherketones, polyphenylene sulfoxide, and combinations thereof.

In another embodiment, the thermoplastic polymer is a thermoplastic elastomer selected from the group consisting of thermoplastic polyurethanes, thermoplastic copolyester, thermoplastic polyamides, and combinations thereof.

In another embodiment, the thermoplastic polymer is selected from the group consisting of polycarbonates, polyolefins, polyimides, polyphthalamide, polyamides, polymethyl methacrylate, polyamideimides, polysulfones, polyethersulfones, polyurethane, polyarylsulfones, poly ketones, polyphenylsulfones, polyetherimides, polyetherketones, polyphenylene sulfoxide, thermoplastic vulcanizate and combinations thereof.

In another embodiment, the thermoplastic polymer is selected from the group consisting of rubber, fiber, plastic, adhesive polymer, polymer paint, polymer composite, engineering plastics, thermoplastic elastomers, and high temperature plastics.

In another embodiment, the thermoplastic polymer is selected from the group consisting of engineering plastics, thermoplastic elastomers, and high temperature plastics.

In another embodiment, the thermoplastic polymer is thermoplastic polyurethane elastomer.

In another embodiment, the polymeric composition further includes at least one selected from the group consisting of glass fibers, carbon fibers, and clays.

In another embodiment, the polymeric composition includes the compound in the amount of between about 0.05 wt % and about 10 wt %. In one embodiment, the polymeric composition includes the compound in the amount of about 0.05 wt %, 0.1 wt %, 0.2 wt %, 0.5 wt %, 1.0 wt %, 1.5 wt %, 2.0 wt %, 5.0 wt %, 10 wt %, 15 wt %, 20 wt %, 25 wt %, or 30 wt %.

In another embodiment, the polymeric composition has a melt flow rate at least 20%, 30%, 40%, 50%, 60%, 70%, 80%, 90%, 100%, 110%, 120%, 130%, 140%, 150%, 160%, 170%, 180%, 190%, or 200% higher than the thermoplastic polymer.

In another embodiment, the compound is selected from the group consisting of

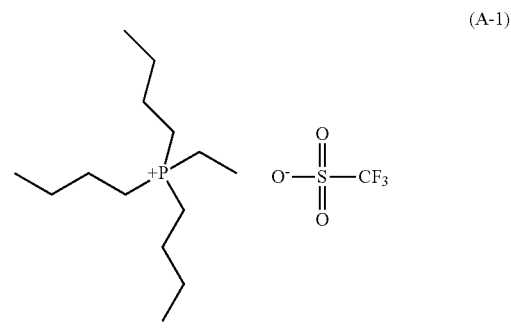

(A-1)

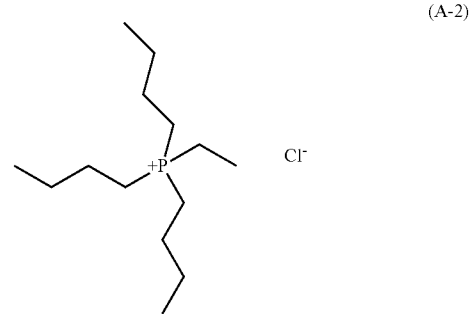

(A-2)

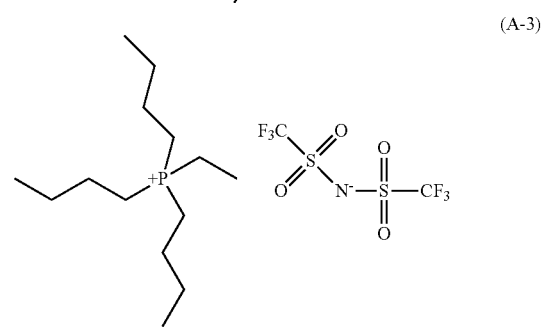

(A-3)

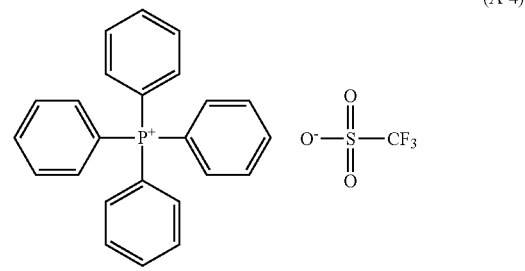

(A-4)

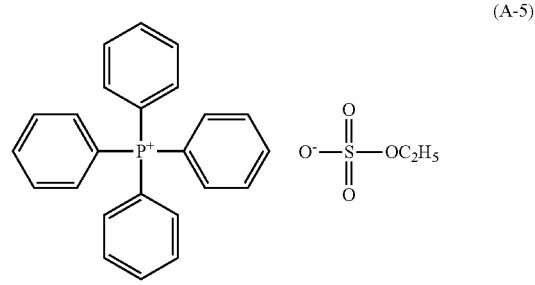

(A-5)

(A-6)
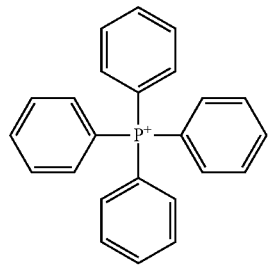
BF$_4^-$ (A-7)
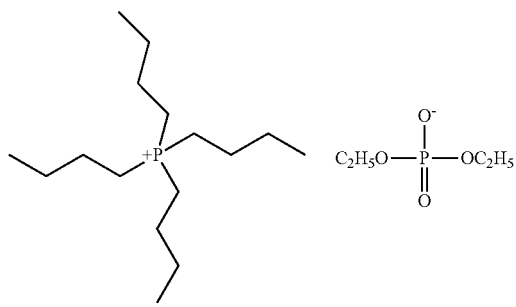

(A-8)
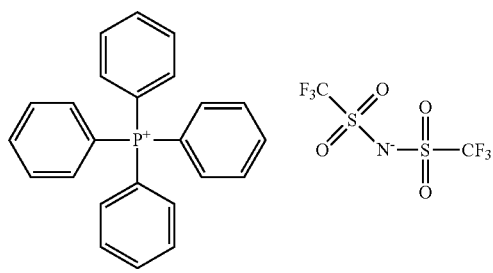

(A-9)
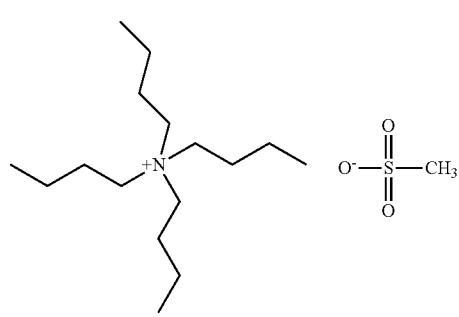

(A-10)
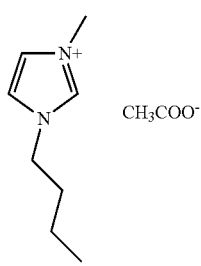
CH$_3$COO$^-$ (A-11)
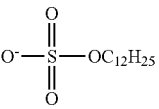
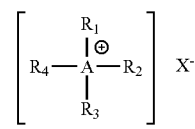

In another aspect, the present disclosure provides a method of preparing a polymeric composition with improved melt flow rate including the step of mixing between about 70 wt % and about 99.99 wt % of a thermoplastic polymer with between about 0.01 wt % and about 30 wt % of a compound having the formula (I)

$$\left[ \begin{array}{c} R_1 \\ | \oplus \\ R_4 - A - R_2 \\ | \\ R_3 \end{array} \right] X^- \qquad (I)$$

wherein A is P or N;

X$^-$ is selected from the group consisting of halide, [B(R)$_4$]$^-$, OH$^-$, SCN$^-$, RPO$_4^-$, (RO)$_2$P(=O)O$^-$, RSO$_3^-$, RSO$_4^-$, ROSO$_3^-$, [N(CN)$_2$]$^-$, RCOO$^-$, NO$_3^-$, [PF$_6$]$^-$, [BF$_4$]$^-$, (RSO$_2$)$_2$N$^-$, oxalate, dicarboxylate and tricarboxylate, formate, phosphate, and aluminate, wherein each R is independently selected from the group consisting of (C$_1$-C$_{20}$)alkyl, aryl, (C$_3$-C$_{10}$)heterocyclyl, (C$_3$-C$_{10}$)cycloalkyl, (C$_3$-C$_{10}$) heterocyclyl(C$_1$-C$_8$)alkyl, aryl(C$_1$-C$_8$)alkyl, heteroaryl and heteroaryl(C$_1$-C$_8$)alkyl group that may be unsubstituted or substituted by halogen, nitro, methoxy, carboxy, —NH$_2$, —OH, —SH, —NHCH$_3$, —N(CH$_3$)$_2$, —SMe and cyano;

when A is P,
  each of R$_1$, R$_2$, R$_3$ and R$_4$ is independently selected from the group consisting of (C$_1$-C$_{20}$)alkyl, aryl, (C$_3$-C$_{10}$) heterocyclyl, (C$_3$-C$_{10}$)cycloalkyl, (C$_3$-C$_{10}$)heterocyclyl (C$_1$-C$_8$) alkyl, aryl(C$_1$-C$_8$)alkyl, heteroaryl and heteroaryl(C$_1$-C$_8$)alkyl that may be unsubstituted or substituted by halogen, nitro, trifluoromethyl, trifluoromethoxy, methoxy, carboxy, —NH$_2$, —OH, —SH, —NHCH$_3$, —N(CH$_3$)$_2$, cyano, —SMe, and —SO$_3$H;

when A is N,
  each of R$_1$, R$_2$, R$_3$ and R$_4$ is independently selected from the group consisting of hydrogen, (C$_1$-C$_{20}$)alkyl, aryl, (C$_3$-C$_{10}$)heterocyclyl, (C$_3$-C$_{10}$)cycloalkyl, (C$_3$-C$_{10}$) heterocyclyl(C$_1$-C$_8$)alkyl, aryl(C$_1$-C$_8$)alkyl, heteroaryl and heteroaryl(C$_1$-C$_8$)alkyl group that may be unsubstituted or substituted by halogen, nitro, trifluoromethyl, trifluoromethoxy, methoxy, carboxy, —NH$_2$, —OH, —SH, —NHCH$_3$, —N(CH$_3$)$_2$, cyano, —SMe, and —SO$_3$H, or

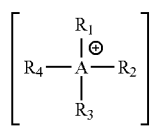

is a heterocyclyl or a heteroaryl ring containing nitrogen, wherein the heterocyclyl or the heteroaryl ring is optionally substituted by a substitution selected the group consisting of $(C_1-C_{20})$alkyl, aryl, $(C_3-C_{10})$heterocyclyl, $(C_3-C_{10})$cycloalkyl, $(C_3-C_{10})$ heterocyclyl $(C_1-C_8)$alkyl, aryl$(C_1-C_8)$alkyl, heteroaryl and heteroaryl$(C_1-C_8)$alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$; wherein the polymeric composition has a melt flow rate higher than that of the thermoplastic polymer.

In one embodiment, when A is P, $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCOO]^-$, $[NO_3]^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, $(C_3-C_{10})$heterocyclyl, $(C_3-C_{10})$cycloalkyl, $(C_3-C_{10})$heterocyclyl$(C_1-C_8)$alkyl, aryl$(C_1-C_8)$alkyl, heteroaryl and heteroaryl$(C_1-C_8)$alkyl group that may be unsubstituted or substituted by halogen, nitro, methoxy, carboxy, —$NH_2$, —OH, —SH, —$NHCH_3$, —$N(CH_3)_2$, —SMe and cyano.

In one embodiment, the thermoplastic polymer is selected from the group consisting of polycarbonates, polyolefins, polyimides, polyphthalamide, polyamides, polymethyl methacrylate, polyamideimides, polysulfones, polyethersulfones, polyurethane, polyarylsulfones, poly ketones, polyphenylsulfones, polyetherimides, polyetherketones, polyphenylene sulfoxide, thermoplastic vulcanizate and combinations thereof.

In another embodiment, the thermoplastic polymer is selected from the group consisting of rubber, fiber, plastic, adhesive polymer, polymer paint, polymer composite, engineering plastics, thermoplastic elastomers, and high temperature plastics.

In another embodiment, the thermoplastic polymer is selected from the group consisting of engineering plastics, thermoplastic elastomers, and high temperature plastics.

In another embodiment, the thermoplastic polymer is a high temperature polymer selected from the group consisting of polyamides, polyamideimides, polysulfones, polyethersulfones, polyarylsulfones, poly ketones, polyphenylsulfones, polyetherimides, polyetherketones, polyphenylene sulfoxide, and combinations thereof.

In another embodiment, the thermoplastic polymer is a thermoplastic elastomer selected from the group consisting of thermoplastic polyurethanes, thermoplastic copolyester, thermoplastic polyamides, and combinations thereof.

In another embodiment, the thermoplastic polymer is thermoplastic polyurethane elastomer.

In another embodiment, each of Ra, $R_2$, $R_3$ or $R_4$ is independently selected from the group consisting of $(C_1-C_{20})$alkyl, aryl, and aryl$(C_1-C_8)$alkyl; $X^-$ is selected from the group consisting of $(CN)_2N^-$, $RCOO^-$, halide, $OH^-$, $SH^-$, $CN^-$, $[PF_6]^-$, $[BF_4]^-$, $ROSO_3^-$, $(RO)_2P(=O)O^-$, and $(RSO_2)_2N^-$, wherein R is selected from the group consisting of $(C_1-C_{20})$alkyl, aryl, and aryl$(C_1-C_8)$alkyl optionally substituted by halogen.

In another embodiment, A is P; each of $R_1$, $R_2$, $R_3$ or $R_4$ is independently selected from the group consisting of $(C_1-C_{20})$alkyl, aryl, and aryl$(C_1-C_8)$alkyl; $X^-$ is selected from the group consisting of $(CN)_2N^-$, $RCOO^-$, halide, $OH^-$, $SH^-$, $CN^-$, $[PF_6]^-$, $[BF_4]^-$, $ROSO_3^-$, $(RO)_2P(=O)O^-$, and $(RSO_2)_2N^-$, wherein R is selected from the group consisting of $(C_1-C_{20})$alkyl, aryl, and aryl$(C_1-C_8)$alkyl optionally substituted by halogen.

In another embodiment, A is N; each of $R_1$, $R_2$, $R_3$ or $R_4$ is independently selected from the group consisting of $(C_1-C_7)$alkyl, aryl, and aryl$(C_1-C_8)$alkyl; or

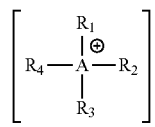

is a heterocyclyl or a heteroaryl ring selected from the group consisting of

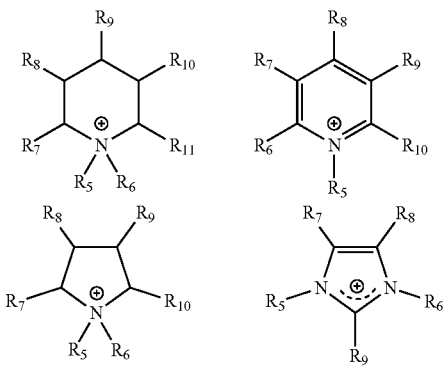

wherein each of $R_5$-$R_{11}$ is independently hydrogen or $(C_1-C_{20})$alkyl;

$X^-$ is selected from the group consisting of $(CN)_2N^-$, $RCOO^-$, halide ion, $OH^-$, $SH^-$, $CN^-$, $[PF_6]^-$, $[BF_4]^-$, $ROSO_3^-$, $RSO_3^-$, $(RO)_2P(=O)O^-$, and $(RSO_2)_2N^-$, wherein R is selected from the group consisting of $(C_1-C_{20})$alkyl, aryl, and aryl$(C_1-C_8)$alkyl optionally substituted by halogen.

In one embodiment, the method includes mixing the compound in the amount of between about 0.05 wt % and about 10 wt % of polymeric composition. In another embodiment, the compound is mixed in the amount of about 0.05 wt %, 0.1 wt %, 0.2 wt %, 0.5 wt %, 1.0 wt %, 1.5 wt %, 2.0 wt %, 5.0 wt %, 10 wt %, 15 wt %, 20 wt %, 25 wt %, or 30 wt % of the polymeric composition.

In one embodiment, the polymeric composition further comprises one selected from the group consisting of glass fibers, carbon fibers, and clays.

In another embodiment, the polymeric composition has a melt flow rate at least 20%, 30%, 40%, 50%, 60%, 70%, 80%, 90%, 100%, 110%, 120%, 130%, 140%, 150%, 160%, 170%, 180%, 190%, or 200% higher than the thermoplastic polymer.

In one embodiment, the preparation of the polymeric compositions disclosed herein is achieved by merely mixing the ingredients under conditions suitable for the formation of an intimate mixture. Such conditions include, but are not limited to, solution blending or melt mixing in single or twin-screw type extruders, mixing bowl, roll, kneader, or similar mixing device that can apply a shear to the components. In one embodiment, a twin-screw extruder is used.

In one embodiment, the compound is selected from the group consisting of compounds A-1, A-2, A-3, A-4, A-5, A-6, A-7, A-8, A-9, A-10, and A-11.

In another aspect, the present disclosure provides a method of preparing a polymeric composition with improved melt flow rate including the step of mixing between about 70 wt % and about 99.99 wt % of a thermoplastic polymer with between about 0.01 wt % and about 30 wt % of a compound having the formula (I) to obtain a polymeric composition;

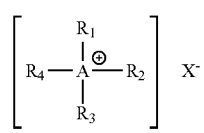
(I)

wherein A is P or N;
when A is P,
  each of $R_1$, $R_2$, $R_3$ and $R_4$ is independently selected from the group consisting of $(C_1-C_{20})$alkyl, aryl, and aryl$(C_1-C_8)$alkyl that may be unsubstituted or substituted by halogen,
  $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCO_2]^-$, $[NO_3]^-$, $R_2PO_4^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, and aryl$(C_1-C_8)$alkyl that may be unsubstituted or substituted by halogen;
when A is N,
  each of $R_1$, $R_2$, $R_3$ and $R_4$ is independently selected from the group consisting of hydrogen, $(C_1-C_{20})$alkyl, aryl, and aryl$(C_1-C_8)$alkyl that may be unsubstituted or substituted by halogen, or

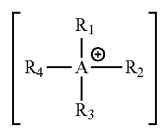

is a heterocyclyl or a heteroaryl ring selected from the group consisting of pyridinium, imidazolium, pyrrolidinium, and piperidinium, wherein the heterocyclyl or the heteroaryl ring is optionally substituted by a substitution selected the group consisting of $(C_1-C_{20})$alkyl, aryl, $(C_3-C_{10})$cycloalkyl, and aryl$(C_1-C_8)$alkyl that may be unsubstituted or substituted by halogen,
  $X^-$ is selected from the group consisting of halide, $[B(R)_4]^-$, $OH^-$, $SCN^-$, $RPO_4^-$, $(RO)_2P(=O)O^-$, $RSO_3^-$, $RSO_4^-$, $ROSO_3^-$, $[N(CN)_2]RCOO^-$, $NO_3^-$, $R_2PO_4^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, aryl$(C_1-C_8)$alkyl that may be unsubstituted or substituted by halogen;

wherein the polymeric composition has a melt flow rate higher than that of the thermoplastic polymer.

Example

The disclosure will now be illustrated with working examples, and which is intended to illustrate the working of disclosure and not intended to restrictively any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Methods

The melt flow index (also called "melt flow rate") was measured by American Society for Testing Materials (ASTM) D1238-04.

Example 1

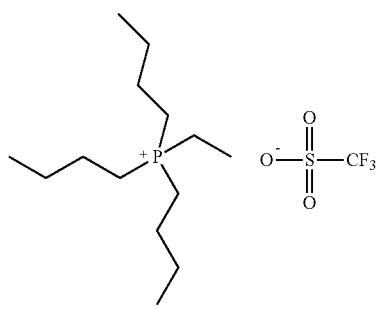
(A-1)

A resin was obtained by mixing 0.5 wt % of compound A-1 with polycarbonate resin using a twin-screw extruder. The resultant resin has a melt flow index increased by 150%. Compound A-1 was also applied in polyamide (Nylon) 6, and Nylon 66. In both cases, the melt flow index increased significantly.

Example 2

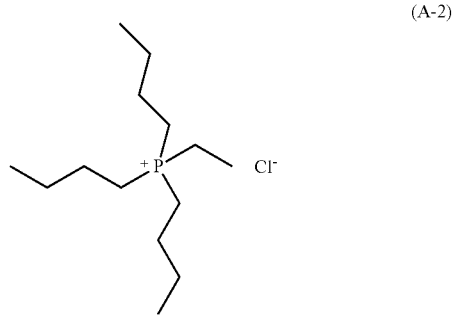
(A-2)

A resin was obtained by mixing 0.3 wt % of compound A-2 with thermoplastic polyurethane (TPU) elastomer using a twin-screw extruder. The resultant modified resin has a melt flow index increased by 60%.

Compound A-2 was applied in other kinds of elastomers, including thermoplastic elastomer (TPE-E, TPE), polyester copolymer elastomer, thermal imide elastomer, thermoplastic elastomer, olefinic (TPO), and thermoplastic vulcanites (TPV). Similar flow improving effects were obtained.

Example 3

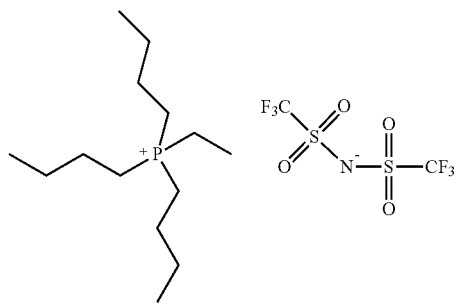

(A-3)

A polymeric composition was obtained by mixing 2 wt % of compound A-3 with polyphthalamide (PPA) using a twin-screw extruder. The torque meter at the extruder showed a reduction: 40%. The melt flow index of the polymeric composition increased by 38% compared to that of original PPA.

Compound A-3 was also applied in other high temperature nylons, including polyamide (PA) 46, PA6T, PA9T, and PA10T. Similar results were obtained.

Example 4

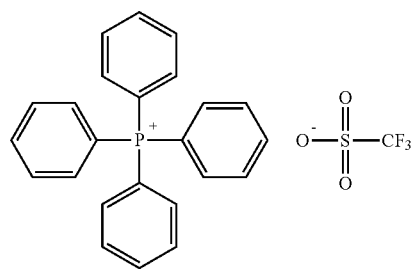

(A-4)

A resin was obtained by mixing 5 wt % of compound A-4 with polysulfone (PSU) using a twin-screw extruder. The resultant resin has a melt flow index increased by 40%.

Compound A-4 was also applied in polyether sulfone (PES), and polyphenylene sulfone (PPSU). Melt flow index increased in every case.

Example 5

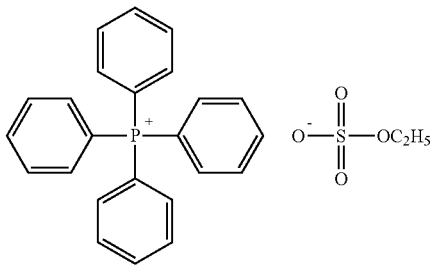

(A-5)

A resin was obtained by mixing 3 wt % of compound A-5 with polyphenylene sulfide (PPS) using a twin-screw extruder. The melt flow index of the resultant resin was 40% higher than that of virgin PPS resin.

Example 6

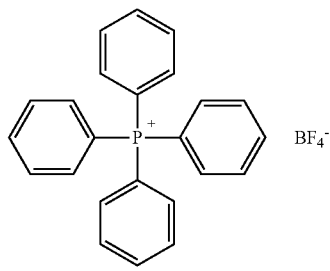

(A-6)

A polymeric composition was obtained by mixing 10 wt % of compound A-6 with polyetheretherketone (PEEK) using a twin-screw extruder. The resultant polymeric composition has a melt index higher than the original PEEK by 36%.

Polyetherketone (PEK) and polyetherketoneketone (PEKK) were also used. The resultant polymeric compositions from both PEK and PEKK have increased melt flow indexes.

Example 7

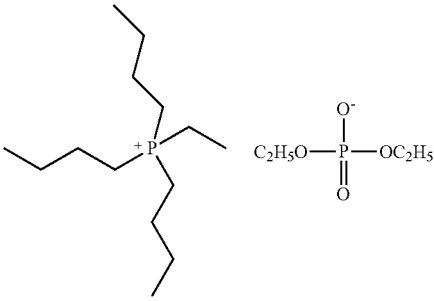

(A-7)

A resin was obtained by mixing 5 wt % of compound A-7 with polybutylene terephthalate (PBT) and 30% glass-fiber using twin-screw extruder. The torque meter on the extruder machine showed a reduction of torque by 30% and the resultant resin has a much smooth surface.

Other polyesters, Polyethylene terephthalate (PET), polytrimethylene terephthalate (PTT), also showed similar effects.

Example 8

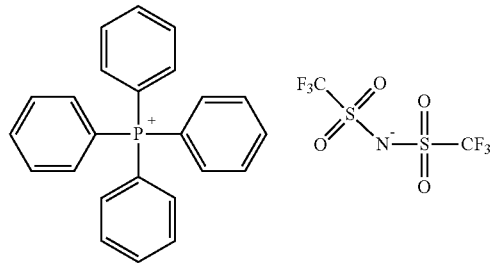

(A-8)

A resin was obtained by mixing 5 wt % of compound A-8 with polyetherimide (PEI) using twin screw extruder. The melt flow index of the resulting resin increased by 35%, compared to original resin. Polyimide (PI) and polyamide-imide (PAI) were also explored, and similar effects were found.

Example 9

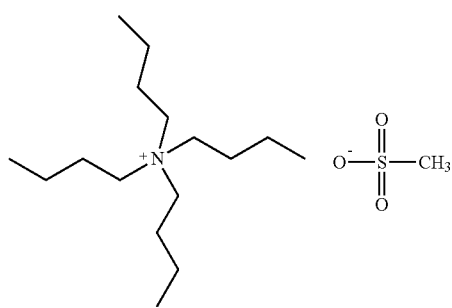

(A-9)

A polymeric composition was obtained by mixing compound A-9 with poly(methyl methacrylate) (PMMA). The resultant polymeric composition is processable at a temperature 20° C. below the temperature for original PMMA.

Similar effects were also observed for cellulose acetate (CA) and cellulose nitrate (CN).

Example 10

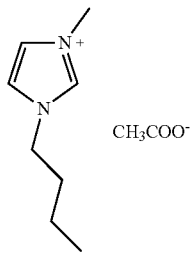

(A-10)

A polymeric composition was obtained by mixing compound A-10 with ethylene-vinyl acetate. The melt flow index of the polymeric composition has increased compared to ethylene-vinyl acetate.

Example 11

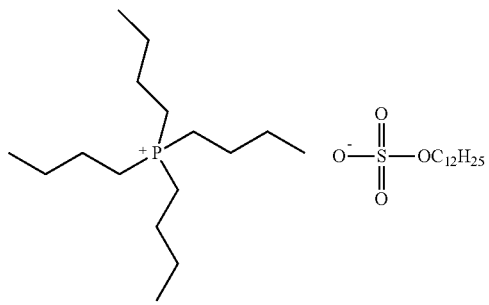

(A-11)

Compound A-11 was applied in polypropylene (PP), polyethylene (PE), polystyrene (PS) and acrylonitrile butadiene styrene (ABS), and their processability was improved.

The present disclosure includes the following embodiments.

Paragraph A-1. A method of preparing a polymeric composition with improved melt flow rate including:

mixing between about 70 wt % and about 99.99 wt % of a thermoplastic polymer with between about 0.01 wt % and about 30 wt % of a compound having the formula (I) to obtain a polymeric composition;

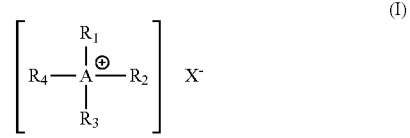

(I)

wherein A is P or N;
$X^-$ is selected from the group consisting of halide, $[B(R)_4]^-$, $OH^-$, $SCN^-$, $RPO_4^-$, $(RO)_2P(=O)O^-$, $RSO_3^-$, $RSO_4^-$, $ROSO_3^-$, $[N(CN)_2]^-$, $RCOO^-$, $NO_3^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1$-$C_{20})$alkyl, aryl, $(C_3$-$C_{10})$heterocyclyl, $(C_3$-$C_{10})$cycloalkyl, $(C_3$-$C_{10})$ heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, methoxy, carboxy, —$NH_2$, —OH, —SH, —$NHCH_3$, —$N(CH_3)_2$, —SMe and cyano; when A is P, each of $R_1$, $R_2$, $R_3$ and $R_4$ is independently selected from the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$)heterocyclyl ($C_1$-$C_8$)alkyl, aryl($C_1$-$C_8$)alkyl, heteroaryl and heteroaryl($C_1$-$C_8$)alkyl that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$; when A is N, each of $R_1$, $R_2$, $R_3$ and $R_4$ is independently selected from the group consisting of hydrogen, ($C_1$-$C_{20}$)alkyl, aryl, ($C_3$-$C_{10}$)heterocyclyl, ($C_3$-$C_{10}$)cycloalkyl, ($C_3$-$C_{10}$)heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, or

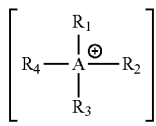

is a heterocyclyl or a heteroaryl ring containing nitrogen, wherein the heterocyclyl or the heteroaryl ring is optionally substituted by a substitution selected the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$) heterocyclyl ($C_1$-$C_8$)alkyl, aryl($C_1$-$C_8$)alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$; wherein the polymeric composition has a melt flow rate higher than that of the thermoplastic polymer.

Paragraph A-2. The method paragraph A-1, wherein when A is P, $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCOO]^-$, $[NO_3]^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$)heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, methoxy, carboxy, —$NH_2$, —OH, —SH, —$NHCH_3$, —$N(CH_3)_2$, —SMe and cyano.

Paragraph A-3. The method of any one of the preceding paragraph, wherein each of $R_1$, $R_2$, $R_3$ or $R_4$ is independently selected from the group consisting of ($C_1$-$C_{20}$)alkyl, aryl, and aryl($C_1$-$C_8$)alkyl; $X^-$ is selected from the group consisting of $(CN)_2N^-$, $RCOO^-$, halide, $OH^-$, $SH^-$, $CN^-$, $[PF_6]^-$, $[BF_4]^-$, $RSO_3^-$, $ROSO_3^-$, $(RO)_2P(=O)O^-$, and $(RSO_2)_2N^-$, wherein R is selected from the group consisting of ($C_1$-$C_{20}$)alkyl, aryl, and aryl($C_1$-$C_8$)alkyl optionally substituted by halogen.

Paragraph A-4. The method of any of the preceding paragraph, wherein A is P;

each of $R_1$, $R_2$, $R_3$ or $R_4$ is independently selected from the group consisting of ($C_1$-$C_{20}$)alkyl, aryl, and aryl ($C_1$-$C_8$)alkyl;

$X^-$ is selected from the group consisting of $(CN)_2N^-$, $RCOO^-$, halide, $OH^-$, $SH^-$, $CN^-$, $[PF_6]^-$, $[BF_4]^-$, $ROSO_3^-$, $(RO)_2P(=O)O^-$, and $(RSO_2)_2N^-$, wherein R is selected from the group consisting of ($C_1$-$C_{20}$)alkyl, aryl, and aryl($C_1$-$C_8$)alkyl optionally substituted by halogen.

Paragraph A-5. The method of any one of the preceding paragraphs, wherein

A is N;

each of $R_1$, $R_2$, $R_3$ or $R_4$ is independently selected from the group consisting of ($C_1$-$C_7$)alkyl, aryl, and aryl($C_1$-$C_8$)alkyl; or

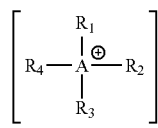

is a heterocyclyl or a heteroaryl ring selected from the group consisting of

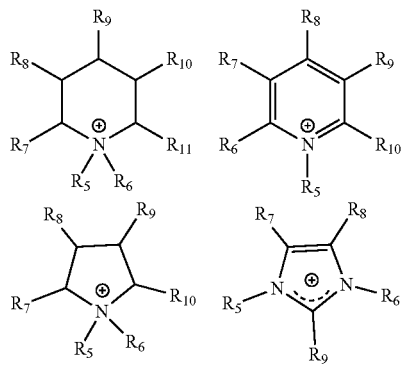

wherein each of $R_5$-$R_{11}$ is independently hydrogen or ($C_1$-$C_{20}$)alkyl, $X^-$ is selected from the group consisting of $(CN)_2N^-$, $RCOO^-$, halide ion, $OH^-$, $SH^-$, $CN^-$, $[PF_6]^-$, $[BF_4]^-$, $ROSO_3^-$, $RSO_3^-$, $(RO)_2P(=O)O^-$, and $(RSO_2)_2N^-$, wherein R is selected from the group consisting of ($C_1$-$C_{20}$)alkyl, aryl, and aryl($C_1$-$C_8$)alkyl optionally substituted by halogen.

Paragraph A-6. A method of preparing a polymeric composition with improved melt flow rate comprising:

mixing between about 70 wt % and about 99.99 wt % of a thermoplastic polymer with between about 0.01 wt % and about 30 wt % of a compound having the formula (I) to obtain a polymeric composition;

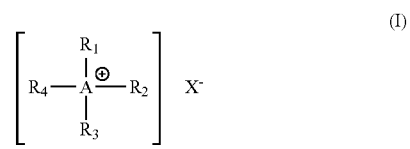
(I)

wherein A is P or N;
when A is P,
   each of $R_1$, $R_2$, $R_3$ and $R_4$ is independently selected from the group consisting of $(C_1-C_{20})$alkyl, aryl, and aryl $(C_1-C_8)$alkyl that may be unsubstituted or substituted by halogen,
   $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCO_2]^-$, $[NO_3]^-$, $R_2PO_4^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, and aryl$(C_1-C_8)$alkyl that may be unsubstituted or substituted by halogen;
when A is N,
   each of $R_1$, $R_2$, $R_3$ and $R_4$ is independently selected from the group consisting of hydrogen, $(C_1-C_{20})$alkyl, aryl, and aryl$(C_1-C_8)$alkyl that may be unsubstituted or substituted by halogen, or

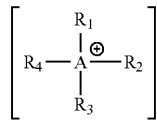

is a heterocyclyl or a heteroaryl ring selected from the group consisting of pyridinium, imidazolium, pyrrolidinium, and piperidinium, wherein the heterocyclyl or the heteroaryl ring is optionally substituted by a substitution selected the group consisting of $(C_1-C_{20})$alkyl, aryl, $(C_3-C_{10})$cycloalkyl, and aryl$(C_1-C_8)$alkyl that may be unsubstituted or substituted by halogen,
   $X^-$ is selected from the group consisting of halide, $[B(R)_4]^-$, $OH^-$, $SCN^-$, $RPO_4^-$, $(RO)_2P(=O)O—$, $RSO_3^-$, $RSO_4^-$, $ROSO_3^-$, $[N(CN)_2]RCOO^-$, $NO_3^-$, $R_2PO_4^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, aryl $(C_1-C_8)$alkyl that may be unsubstituted or substituted by halogen;
wherein the polymeric composition has a melt flow rate higher than that of the thermoplastic polymer.

Paragraph A-7. A method of preparing a polymeric composition with improved melt flow rate including:
   mixing between about 70 wt % and about 99.99 wt % of a thermoplastic polymer with between about 0.01 wt % and about 30 wt % of a compound selected from the group consisting of

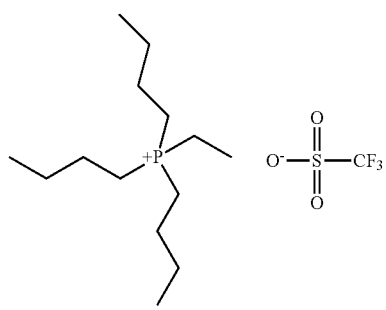
(A-1)

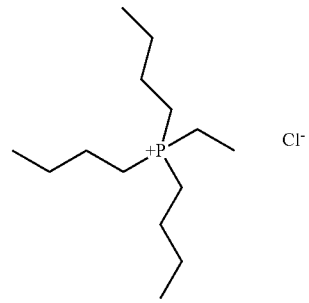
(A-2)

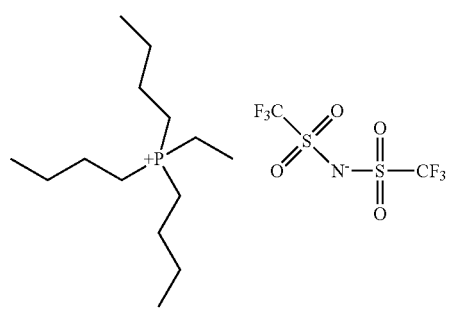
(A-3)

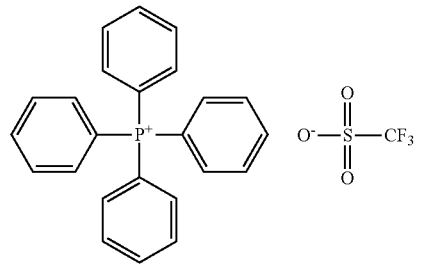
(A-4)

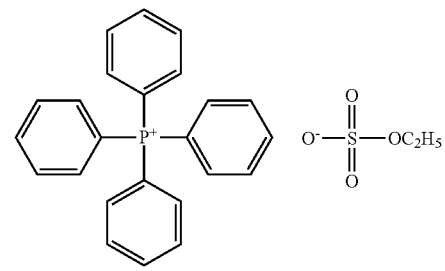
(A-5)

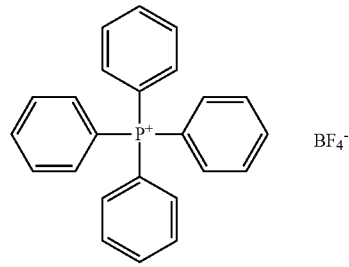
(A-6)

-continued

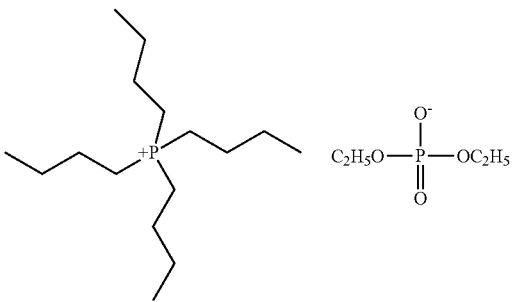
(A-7)

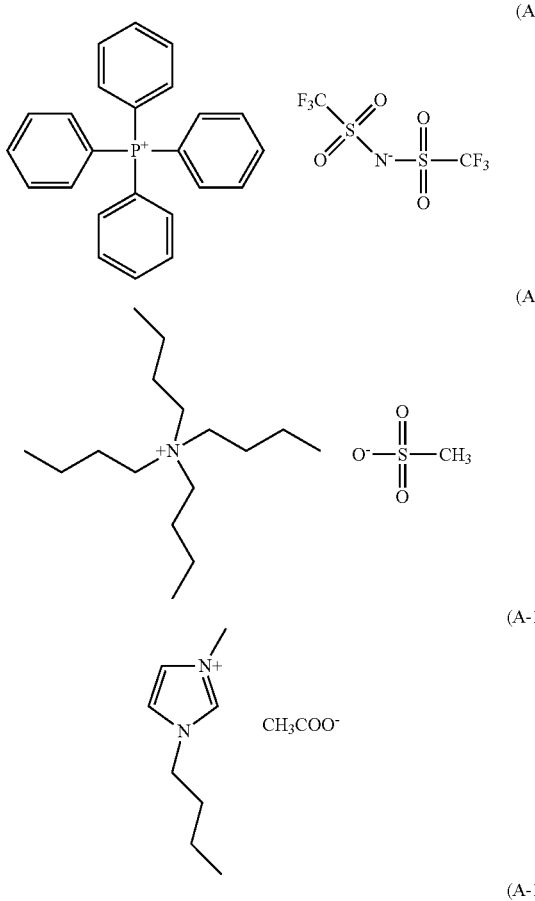
(A-8)

(A-9)

(A-10)

(A-11)

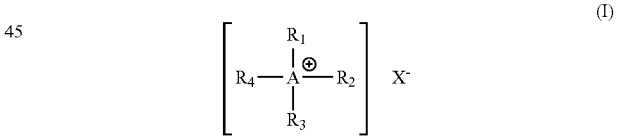

Paragraph A-8. The method of any one of the preceding paragraphs, wherein the thermoplastic polymer is selected from the group consisting of polycarbonates, polyolefins, polyimides, polyphthalamide, polyamides, polymethyl methacrylate, polyamideimides, polysulfones, polyethersulfones, polyurethane, polyarylsulfones, poly ketones, polyphenylsulfones, polyetherimides, polyetherketones, polyphenylene sulfoxide, thermoplastic vulcanizate and combinations thereof; or the thermoplastic polymer is selected from the group consisting of rubber, fiber, plastic, adhesive polymer, polymer paint, polymer composite, engineering plastics, thermoplastic elastomers, and high temperature plastics; or the thermoplastic polymer is selected from the group consisting of engineering plastics, thermoplastic elastomers, and high temperature plastics.

Paragraph A-9. The method of any one of the preceding paragraphs, wherein the thermoplastic polymer is a high temperature polymer selected from the group consisting of polyamides, polyamideimides, polysulfones, polyethersulfones, polyarylsulfones, poly ketones, polyphenylsulfones, polyetherimides, polyetherketones, polyphenylene sulfoxide, and combinations thereof.

Paragraph A-10. The method of any one of the preceding paragraphs, wherein the thermoplastic polymer is a thermoplastic elastomer selected from the group consisting of thermoplastic polyurethanes, thermoplastic copolyester, thermoplastic polyamides, and combinations thereof.

Paragraph A-11. The method of any one of the preceding paragraphs, wherein the thermoplastic polymer is thermoplastic polyurethane elastomer.

Paragraph A-12. The method of any one of the preceding paragraphs, including mixing between about 0.05 wt % and about 10 wt % of the compound.

Paragraph A-13. The method of any one of the preceding paragraphs, wherein the polymeric composition further includes one selected from the group consisting of glass fibers, carbon fibers, and clays.

Paragraph A-14. The method of any one of the preceding paragraphs, wherein the polymeric composition has a melt flow rate at least 20% higher than the thermoplastic polymer, optionally, the polymeric composition has a melt flow rate at least 60% higher than the thermoplastic polymer.

Paragraph A-15. A polymeric composition including,
  between about 70 wt % and about 99.99 wt % of a thermoplastic polymer; and
  between about 0.01 wt % and about 30 wt % of a compound having the formula of $$\left[ \begin{array}{c} R_1 \\ | \\ R_4 - A^{\oplus} - R_2 \\ | \\ R_3 \end{array} \right] X^- \quad (I)$$

wherein A is P or N;
X$^-$ is selected from the group consisting of halide, [B(R)$_4$]$^-$, OH$^-$, SCN$^-$, RPO$_4^-$, (RO)$_2$P(=O)O$^-$, RSO$_3^-$, RSO$_4^-$, ROSO$_3^-$, [N(CN)$_2$]$^-$, RCOO$^-$, NO$_3^-$, [PF$_6$]$^-$, [BF$_4$]$^-$, (RSO$_2$)$_2$N$^-$, oxalate, dicarboxylate and tricarboxylate, formate, phosphate, and aluminate, wherein each R is independently selected from the group consisting of (C$_1$-C$_{20}$)alkyl, aryl, (C$_3$-C$_{10}$)heterocyclyl, (C$_3$-C$_{10}$)cycloalkyl, (C$_3$-C$_{10}$) heterocyclyl(C$_1$-C$_8$)alkyl, aryl(C$_1$-C$_8$)alkyl, heteroaryl and heteroaryl(C$_1$-C$_8$)alkyl group that may be unsubstituted or substituted by halogen, nitro, methoxy, carboxy, —NH$_2$, —OH, —SH, —NHCH$_3$, —N(CH$_3$)$_2$, —SMe and cyano;
when A is P,
  each of R$_1$, R$_2$, R$_3$ and R$_4$ is independently selected from the group consisting of (C$_1$-C$_{20}$)alkyl, aryl, (C$_3$-C$_{10}$) heterocyclyl, (C$_3$-C$_{10}$)cycloalkyl, (C$_3$-C$_{10}$)heterocyclyl (C$_1$-C$_8$) alkyl, aryl(C$_1$-C$_8$)alkyl, heteroaryl and heteroaryl($C_1$-$C_8$)alkyl that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$;

when A is N, each of $R_1$, $R_2$, $R_3$ and $R_4$ is independently selected from the group consisting of hydrogen, ($C_1$-$C_{20}$)alkyl, aryl, ($C_3$-$C_{10}$)heterocyclyl, ($C_3$-$C_{10}$)cycloalkyl, ($C_3$-$C_{10}$) heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, or

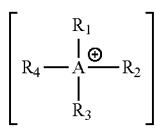

is a heterocyclyl or a heteroaryl ring containing nitrogen, wherein the heterocyclyl or the heteroaryl ring is optionally substituted by a substitution selected the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$) heterocyclyl ($C_1$-$C_8$)alkyl, aryl($C_1$-$C_8$)alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$;

wherein the thermoplastic polymer is a high temperature polymer selected from the group consisting of polyamides, polyamideimides, polysulfones, polyethersulfones, polyarylsulfones, poly ketones, polyphenylsulfones, polyetherimides, polyetherketones, polyphenylene sulfoxide, and combinations thereof; or the thermoplastic polymer is a thermoplastic elastomer selected from the group consisting of thermoplastic polyurethanes, thermoplastic copolyester, thermoplastic polyamides, and combinations thereof;

wherein the polymeric composition has a melt flow rate higher than that of the thermoplastic polymer;

optionally the compound is selected from the group consisting of

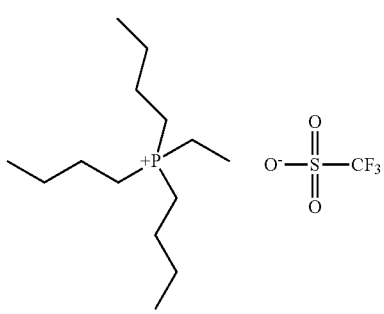
(A-1)

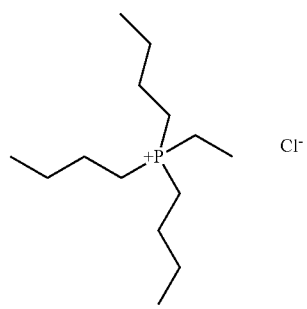
(A-2)

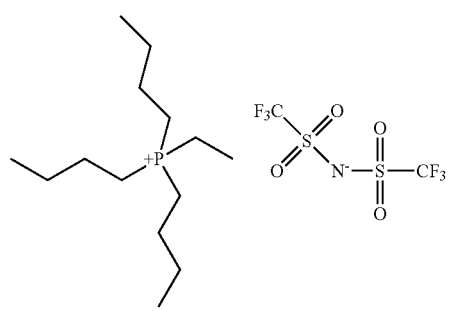
(A-3)

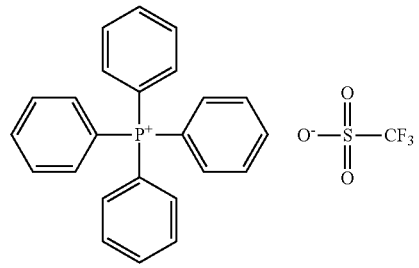
(A-4)

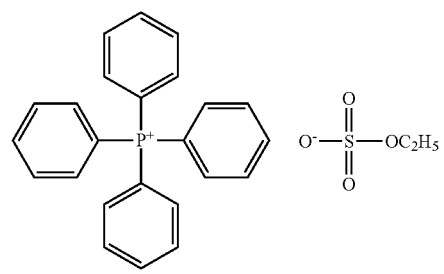
(A-5)

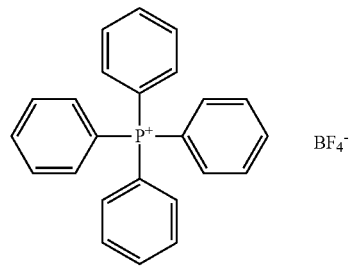
(A-6)

-continued

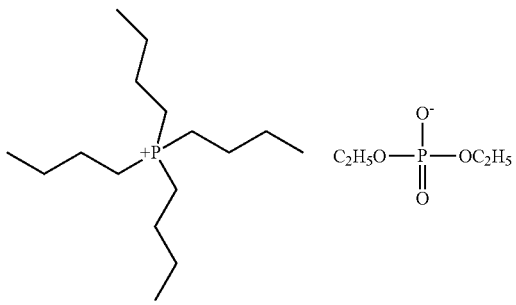 (A-7)

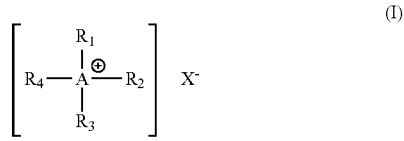

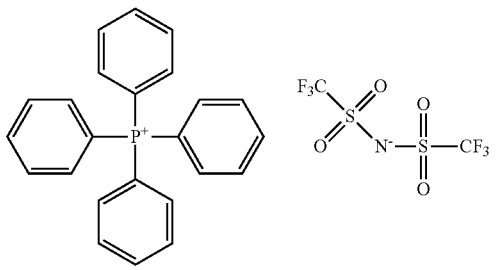 (A-8)

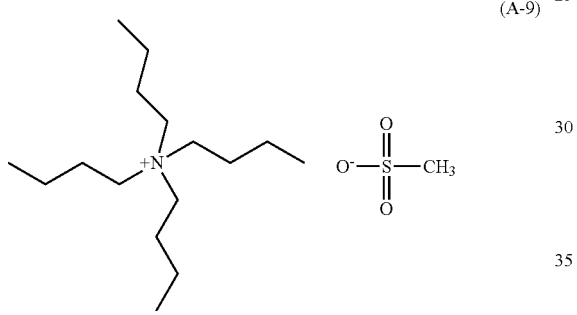 (A-9)

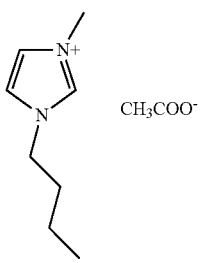 (A-10)

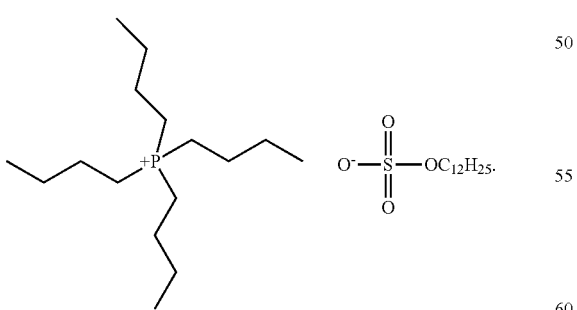 (A-11)

We claim:

1. A method of preparing a polymeric composition with improved melt flow rate consisting of:
mixing between about 70 wt % and about 99.99 wt % of one thermoplastic polymer with between about 0.01 wt % and about 5 wt % of a compound having the formula (I) to obtain a polymeric composition;
optionally mixing one selected from the group consisting of glass fibers, carbon fibers, and clays into the polymeric composition;

$$\left[ R_4 - \overset{R_1}{\underset{R_3}{\overset{\oplus}{A}}} - R_2 \right] X^- \quad (I)$$

wherein A is P or N;
when A is P,
each of $R_1$, $R_2$, $R_3$ and $R_4$ is independently selected from the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$) heterocyclyl($C_1$-$C_8$) alkyl, aryl($C_1$-$C_8$)alkyl, heteroaryl and heteroaryl($C_1$-$C_8$)alkyl that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$;
$X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCOO]^-$, $[NO_3]^-$, $[PF_6]^-$, $[BF]^-$, $(RSO_2)_2N^-$, oxalate, dicarboxylate and tricarboxylate, formate, phosphate, and aluminate, wherein each R is independently selected from the group consisting of ($C_1$-$C_{20}$)alkyl, aryl, ($C_3$-$C_{10}$) heterocyclyl, ($C_3$-$C_{10}$)cycloalkyl, ($C_3$-$C_{10}$)heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, methoxy, carboxy, —$NH_2$, —OH, —SH, —$NHCH_3$, —$N(CH_3)_2$, —SMe and cyano;
when A is N,
each of $R_1$, $R_2$, $R_3$ and $R_4$ is independently selected from the group consisting of hydrogen, ($C_1$-$C_{20}$) alkyl, aryl, ($C_3$-$C_{10}$)heterocyclyl, ($C_3$-$C_{10}$)cycloalkyl, ($C_3$-$C_{10}$) heterocyclyl($C_1$-$C_8$)alkyl, aryl($C_1$-$C_8$) alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$, or $$\left[ R_4 - \overset{R_1}{\underset{R_3}{\overset{\oplus}{A}}} - R_2 \right]$$

is a heterocyclyl or a heteroaryl ring containing nitrogen, wherein the heterocyclyl or the heteroaryl ring is optionally substituted by a substitution selected the group consisting of ($C_1$-$C_{20}$)alkyl, aryl, ($C_3$-$C_{10}$)heterocyclyl, ($C_3$-$C_{10}$)cycloalkyl, ($C_3$-$C_{10}$) heterocyclyl($C_1$-$C_8$)alkyl, aryl($C_1$-$C_8$)alkyl, heteroaryl and heteroaryl($C_1$-$C_8$)alkyl group that may be unsubstituted or substituted by halogen, nitro, trifluoromethyl, trifluoromethoxy, methoxy, carboxy, —$NH_2$, —OH, —SH, —$NHCH_3$, —$N(CH_3)_2$, cyano, —SMe, and —$SO_3H$;
$X^-$ is selected from the group consisting of halide, $[B(R)_4]^-$, $OH^{31}$, $SCN^-$, $RPO_4^-$, $(RO)_2P(=O)O^-$, RSO$_3^-$, RSO$_4^-$, ROSO$_3^-$, [N(CN)$_2$]$^-$, RCOO$^-$, NO$_3^-$, [PF$_6$]$^-$, [BF$_4$]$^-$, (RSO$_2$)$_2$N$^-$, oxalate, dicarboxylate and tricarboxylate, formate, phosphate, and aluminate, wherein each R is independently selected from the group consisting of (C$_1$-C$_{20}$)alkyl, aryl, (C$_3$-C$_{10}$)heterocyclyl, (C$_3$-C$_{10}$)cycloalkyl, (C$_3$-C$_{10}$)heterocyclyl(C$_1$-C$_8$)alkyl, aryl(C$_1$-C$_8$)alkyl, heteroaryl and heteroaryl(C$_1$-C$_8$)alkyl group that may be unsubstituted or substituted by halogen, nitro, methoxy, carboxy, —NH$_2$, —OH, —SH, —NHCH$_3$, —N(CH$_3$)$_2$, —SMe and cyano;

wherein the polymeric composition has a melt flow rate higher than that of the thermoplastic polymer; and wherein the thermoplastic polymer is thermoplastic polyurethane elastomer.

2. The method of claim 1, wherein

A is P;

each of R$_1$, R$_2$, R$_3$ or R$_4$ is independently selected from the group consisting of (C$_1$-C$_{20}$)alkyl, aryl, and aryl(C$_1$-C$_8$)alkyl;

X$^-$ is selected from the group consisting of (CN)$_2$N$^-$, RCOO$^-$, halide, OH$^-$, SH$^-$, CN$^-$, [PF$_6$]$^-$, [BF$_4$]$^-$, ROSO$_3^-$, (RO)$_2$P(=O)O$^-$, and (RSO$_2$)$_2$N$^-$, wherein R is selected from the group consisting of (C$_1$-C$_{20}$)alkyl, aryl, and aryl(C$_1$-C$_8$)alkyl optionally substituted by halogen.

3. The method of claim 1, wherein

A is N;

each of R$_1$, R$_2$, R$_3$ or R$_4$ is independently selected from the group consisting of (C$_1$-C$_7$)alkyl, aryl, and aryl(C$_1$-C$_8$)alkyl; or

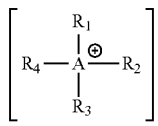

is a heterocyclyl or a heteroaryl ring selected from the group consisting of

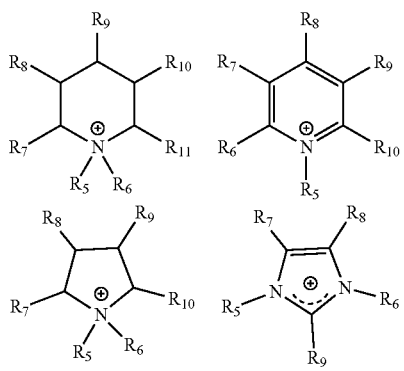

wherein each of R$_5$-R$_{11}$ is independently hydrogen or (C$_1$-C$_{20}$)alkyl;

X$^-$ is selected from the group consisting of (CN)$_2$N$^-$, RCOO$^-$, halide ion, OH$^{31}$, SH$^-$, CN$^-$, [PF$_6$]$^-$, [BF$_4$]$^-$, ROSO$_3^-$, RSO$_3^-$, (RO)$_2$P(=O)O$^-$, and (RSO$_2$)$_2$N$^-$, wherein R is selected from the group consisting of (C$_1$-C$_{20}$)alkyl, aryl, and aryl(C$_1$-C$_8$)alkyl optionally substituted by halogen.

4. The method of claim 1, wherein the polymeric composition has a melt flow rate at least 60% higher than the thermoplastic polymer.

5. The method of claim 1, wherein a twin-screw extruder is used in mixing.

6. The method of claim 1, wherein the compound is selected from the group consisting of

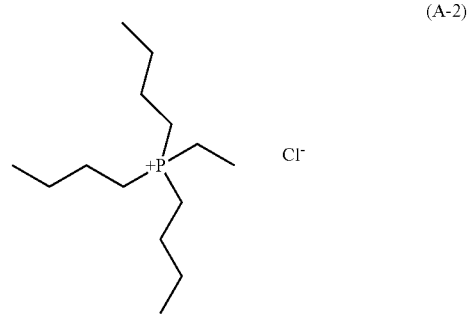
(A-2)

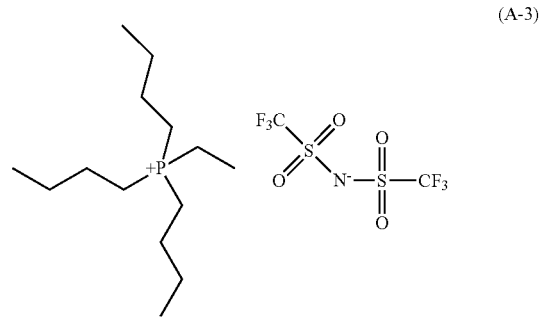
(A-3)

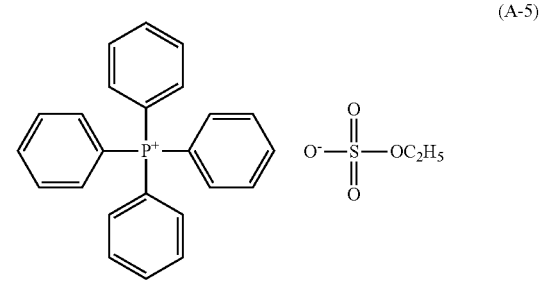
(A-5)

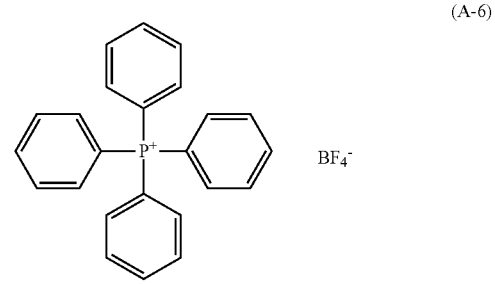
(A-6)

-continued

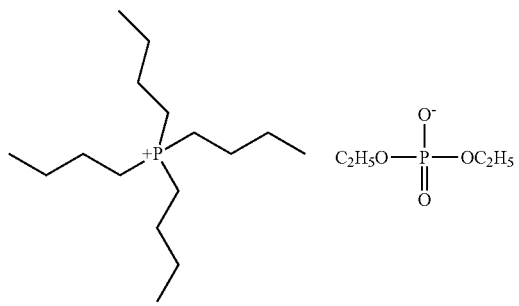 (A-7)

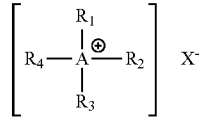

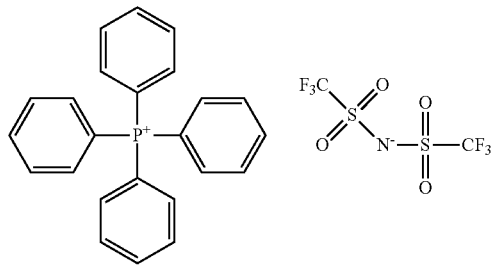 (A-8)

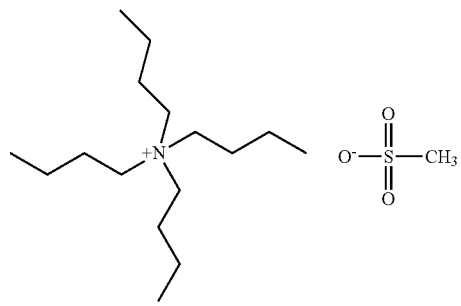 (A-9)

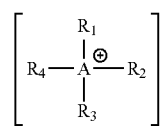

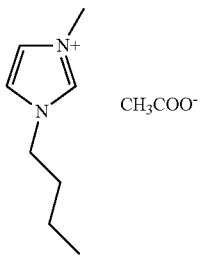 (A-10)

CH₃COO⁻

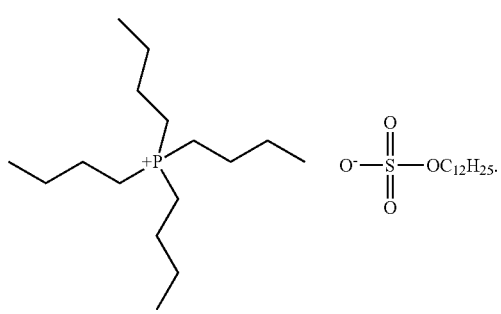 (A-11)

7. A method of preparing a polymeric composition with improved melt flow rate consisting of:

mixing between about 70 wt % and about 99.99 wt % of one thermoplastic polymer with between about 0.01 wt % and about 5 wt % of a compound having the formula (I) to obtain a polymeric composition;

optionally mixing one selected from the group consisting of glass fibers, carbon fibers, and clays into the polymeric composition;

$$\left[ R_4 - \overset{R_1}{\underset{R_3}{\overset{\oplus}{A}}} - R_2 \right] X^-$$ (I)

wherein A is P or N;

when A is P,
each of $R_1$, $R_2$, $R_3$ and $R_4$ is independently selected from the group consisting of $(C_1-C_{20})$alkyl, aryl, and aryl$(C_1-C_8)$alkyl that may be unsubstituted or substituted by halogen, $X^-$ is selected from the group consisting of halide, $[B(R)_4]^-$, $OH^-$, $SCN^-$, $RPO_4^-$, $(RO)_2P(=O)O^-$, $RSO_4^-$, $ROSO_3^-$, $[N(CN)_2]^-$, $[RCO_2]^-$, $[NO_3]^-$, $R_2PO_4^-$, $[PF_6]^-$, $[BF_4]^-$, $(RSO_2)_2N$, oxalate, dicarboxylate and tricarboxylate, formate, phosphate, and aluminate, wherein each R is independently selected from the group consisting of $(C_1-C_{20})$alkyl, aryl, and aryl$(C_1-C_8)$alkyl that may be unsubstituted or substituted by halogen;

when A is N,
each of $R_1$, $R_2$, $R_3$ and $R_4$ is independently selected from the group consisting of hydrogen, $(C_1-C_{20})$ alkyl, aryl, and aryl$(C_1-C_8)$alkyl that may be unsubstituted or substituted by halogen, or $$\left[ R_4 - \overset{R_1}{\underset{R_3}{\overset{\oplus}{A}}} - R_2 \right]$$

is a heterocyclyl or a heteroaryl ring selected from the group consisting of pyridinium, imidazolium, pyrrolidinium, and piperidinium, wherein the heterocyclyl or the heteroaryl ring is optionally substituted by a substitution selected the group consisting of $(C_1-C_{20})$alkyl, aryl, $(C_3-C_{10})$cycloalkyl, and aryl$(C_1-C_8)$alkyl that may be unsubstituted or substituted by halogen, $X^-$ is selected from the group consisting of halide, $[B(R)_4]^-$, $OH^-$, $SCN^-$, $RPO_4^-$, $(RO)_2P(=O)O^-$, $RSO_3^-$, $RSO_4^-$, $ROSO_3^-$, $[N(CN)_2]^-$, $RCOO^-$, $NO_3^-$, $R_2PO_4^-$, $[PF_6]^-$, $[BF_4]^-$, $(RSO_2)_2N^-$, oxalate, dicarboxylate and tricarboxylate, formate, phosphate, and aluminate, wherein each R is independently selected from the group consisting of $(C_1-C_{20})$alkyl, aryl, aryl$(C_1-C_8)$alkyl that may be unsubstituted or substituted by halogen;

wherein the polymeric composition has a melt flow rate higher than that of the thermoplastic polymer; and wherein the thermoplastic polymer is thermoplastic polyurethane elastomer.

* * * * *